US009623117B2

(12) United States Patent
Chapman et al.

(10) Patent No.: US 9,623,117 B2
(45) Date of Patent: Apr. 18, 2017

(54) METHOD FOR SELECTIVE TARGETING AND ENTRY OF BACTERIAL TOXINS TO CELLS

(75) Inventors: Edwin Raymond Chapman, Madison, WI (US); Felix Leejia Yeh, San Francisco, CA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 303 days.

(21) Appl. No.: 13/435,688

(22) Filed: Mar. 30, 2012

(65) Prior Publication Data

US 2015/0283261 A1 Oct. 8, 2015

Related U.S. Application Data

(60) Provisional application No. 61/471,406, filed on Apr. 4, 2011.

(51) Int. Cl.
*A61K 39/00* (2006.01)
*A61K 47/48* (2006.01)

(52) U.S. Cl.
CPC .. *A61K 47/48484* (2013.01); *A61K 47/48561* (2013.01)

(58) Field of Classification Search
CPC ...... A61K 39/395; A61K 38/00; A61K 51/06; A61K 47/48484; C12N 15/12; C07K 17/00
USPC ...................................................... 424/179.1
See application file for complete search history.

(56) References Cited

U.S. PATENT DOCUMENTS

| | | | | |
|---|---|---|---|---|
| 4,676,980 A * | 6/1987 | Segal et al. | ................. | 424/136.1 |
| 4,752,638 A * | 6/1988 | Nowinski et al. | ........... | 525/54.1 |
| 5,616,690 A * | 4/1997 | Axworthy | ........ | A61K 47/48023 530/363 |
| 5,863,745 A * | 1/1999 | Fitzgerald | ........ | A61K 47/48369 424/134.1 |
| 6,099,842 A * | 8/2000 | Pastan | ................... | C07K 14/21 424/178.1 |
| 6,214,974 B1 * | 4/2001 | Rosenblum | ...... | A61K 47/48753 424/172.1 |
| 6,217,869 B1 * | 4/2001 | Meyer et al. | .............. | 424/178.1 |
| 6,395,276 B1 * | 5/2002 | Rybak | .............. | A61K 47/48438 424/134.1 |
| 6,423,513 B1 * | 7/2002 | Fitzgerald et al. | .......... | 435/71.3 |
| 6,426,075 B1 * | 7/2002 | Fitzgerald | ........ | A61K 47/48484 424/183.1 |
| 6,497,881 B1 * | 12/2002 | Meruelo | .......... | A61K 47/48438 424/130.1 |
| 7,208,174 B2 * | 4/2007 | Huwyler | .............. | A61K 9/1271 424/450 |
| 7,405,320 B2 * | 7/2008 | McBride et al. | ................ | 560/41 |
| 7,736,647 B2 * | 6/2010 | Boumsell | ......... | A61K 47/48561 424/1.49 |
| 7,807,780 B2 * | 10/2010 | Waugh et al. | ................. | 530/327 |
| 8,936,792 B2 * | 1/2015 | Pastan | .................... | C07K 14/21 424/185.1 |
| 8,987,426 B2 * | 3/2015 | Neville, Jr. | ...... | A61K 47/48484 530/391.7 |
| 2002/0081303 A1 * | 6/2002 | Hott | ................. | A61K 47/48446 424/178.1 |
| 2002/0187153 A1 * | 12/2002 | Goldenberg | ..... | A61K 47/48484 424/179.1 |
| 2003/0096748 A1 * | 5/2003 | Holoshitz | .............. | A61K 38/08 424/178.1 |
| 2003/0165853 A1 * | 9/2003 | Partridge | ......... | A61K 47/48246 435/6.16 |
| 2003/0229034 A1 * | 12/2003 | Waugh et al. | .................. | 514/44 |
| 2004/0018203 A1 * | 1/2004 | Pastan et al. | .............. | 424/178.1 |
| 2004/0102369 A1 * | 5/2004 | Wu | ..................... | A61K 38/1825 424/141.1 |
| 2005/0085419 A1 * | 4/2005 | Morrison | ............. | C07K 14/465 435/69.1 |
| 2005/0142141 A1 * | 6/2005 | Pardridge | ........ | A61K 47/48561 424/178.1 |
| 2005/0276756 A1 * | 12/2005 | Hoo | ..................... | A61K 31/704 424/1.49 |
| 2006/0193771 A1 * | 8/2006 | Pastan | .............. | A61K 47/48484 424/1.49 |

(Continued)

FOREIGN PATENT DOCUMENTS

| | | | | |
|---|---|---|---|---|
| WO | 94/04702 | * | 3/1994 | |
| WO | 97/19957 | * | 6/1997 | ............. C07K 17/00 |

(Continued)

OTHER PUBLICATIONS

Kang, Y et al, The Journal of Pharmacology and Experimental Therapeutics, vol. 269(1), pp. 344-350, Use of Neutral Avidin Improves Pharmacokinetics and Brain Delivery of Biotin Bound to an Avidin Monoclonal Antibody conjugate.*
Penichet, ML et al, The Journal of Immunology, vol. 163, pp. 4421-44265, 1999, An Antibody-Avidin Fusion Protein Specific to the Transferrin Receptor Serves as a Delivery Vehicle for Effective Brain Targeting: Initial Applications in Anti-HIV Antisense Drug Delivery to the Brain.*
Cameron, PL et al, The Journal of Cell Biology, vol. 115(1), Oct. 1991, pp. 151-164.*
Aoki, Review of a Proposed Mechanism for the Antinociceptive Action of Botulinum Toxin Type A, Neurotoxicology, 2005, 26(5):785-793.

(Continued)

*Primary Examiner* — Albert Navarro
(74) *Attorney, Agent, or Firm* — Quarles & Brady, LLP

(57) ABSTRACT

The present invention provides methods and reagents for directing the selective targeting and entry of bacterial toxins to mammalian cells. Methods include the step of contacting a cell with a bacterial toxin or toxic bioactive fragment thereof associated with an antibody or ligand that is specific to a target on the cell, wherein the antibody or ligand selectively binds the target on the cell and the bacterial toxin or fragment thereof is internalized and enters the cell. The invention further encompasses compositions and kits to carry out the methods.

10 Claims, 6 Drawing Sheets

(56) References Cited

U.S. PATENT DOCUMENTS

| | | | | |
|---|---|---|---|---|
| 2006/0263368 | A1* | 11/2006 | Rosenblum | A61K 41/0038 424/155.1 |
| 2006/0286030 | A1* | 12/2006 | Boumsell | A61K 47/48561 424/1.49 |
| 2007/0141070 | A1* | 6/2007 | Mrsny | A61K 39/395 424/178.1 |
| 2007/0189962 | A1* | 8/2007 | Pastan | A61K 47/48484 424/1.49 |
| 2008/0070278 | A1* | 3/2008 | North et al. | 435/69.1 |
| 2009/0011984 | A1* | 1/2009 | Yla-Herttuala et al. | 514/12 |
| 2009/0175789 | A1* | 7/2009 | Behrens et al. | 424/9.1 |
| 2009/0220501 | A1* | 9/2009 | Fey | A61K 47/48484 424/133.1 |
| 2009/0285808 | A1* | 11/2009 | Tedder et al. | 424/133.1 |
| 2010/0098706 | A1* | 4/2010 | De Romeuf et al. | 424/144.1 |
| 2010/0189649 | A1* | 7/2010 | Greene et al. | 424/9.1 |
| 2011/0086768 | A1* | 4/2011 | Turner | C07K 14/705 506/9 |
| 2011/0129413 | A1* | 6/2011 | Morgan | A61K 41/0057 424/1.29 |
| 2011/0189209 | A1* | 8/2011 | Neville et al. | 424/183.1 |
| 2011/0250199 | A1* | 10/2011 | Fitzgerald | A61K 47/48484 424/134.1 |
| 2011/0262991 | A1* | 10/2011 | Raja | A61K 47/4813 435/188 |
| 2011/0270152 | A1* | 11/2011 | Atanasoska | A61L 29/16 604/20 |
| 2012/0258126 | A1* | 10/2012 | Scholler et al. | 424/186.1 |
| 2013/0202652 | A1* | 8/2013 | Manoharan | A61K 47/48023 424/278.1 |
| 2014/0065142 | A1* | 3/2014 | Roschke | C07K 16/2848 424/134.1 |
| 2014/0193358 | A1* | 7/2014 | Merchant | A61K 47/48261 424/85.2 |

FOREIGN PATENT DOCUMENTS

| | | | | |
|---|---|---|---|---|
| WO | 99/42577 | * | 8/1999 | C12N 15/12 |
| WO | 02/17968 | * | 3/2002 | A61K 48/00 |
| WO | 2005/084361 | * | 9/2005 | |
| WO | 2008/082885 | * | 7/2008 | A61K 51/06 |
| WO | 2008/097817 | * | 8/2008 | C07K 16/28 |
| WO | 2011/031441 | * | 3/2011 | A61K 31/495 |
| WO | 2011/032022 | * | 3/2011 | A61K 47/48 |

OTHER PUBLICATIONS

Chaddock, et al., Expression and Purification of Catalytically Active, Non-Toxic Endopeptidase Derivatives of Clostridium Botulinum Toxin Type A, Protein Expression and Purification, 2002, 25(2):219-228.
Chapman, How Does Synaptotagmin Trigger Neurotransmitter Release?, Annu. Rev. Biochem., 2008, 77:615-641.
Davis, et al., Regulated Airway Goblet Cell Mucin Secretion, Annu. Rev. Physiol., 2008, 70:487-512.
Dolly, et al., The Structure and Mode of Action of Different Botulinum Toxins, Eur. J. Neurol., 2006, 13(Suppl 4):1-9.
Dong, et al., SV2 is the Protein Receptor for Botulinumn Neurotoxin A, Science, 2006, 312:592-596.
Dong, et al., Mechanism of Botulinum Neurotoxin B and G Entry Into Hippocampal Neurons, Journal of Cell Biology, 2007, 179:1511-1522.
Dong, et al., Glycosylated SV2A and SV2B Mediate the Entry of Botulinum Neurotoxin E Into Neurons, Molecular Biology of the Cell, 2008, 19:5226-5237.
Fujihara, et al., Inhibition of NF-kappaB by a Cell Permeable Form of IkappaBAlpha Induces Apoptosis in Eosinophils, Biochemical and Biophysical Research Communications, 2005, 326(3):632-637.
Gavala, et al., The Nucleotide Receptor P2RX7 Mediates ATP-Induced CREB Activation in Human and Murine Monocytic Cells, Journal of Leukocyte Biology, 2008, 84:1159-1171.
Geppert, et al., Synaptotagmin II. A Novel Differentially Distributed Form of Synaptotagmin., Journal of Biological Chemistry, 1991, 266:13548-13552.
Helting, et al., Toxicity of Papain-Digested Tetanus Toxin. Pathological Effect of Fragment B in the Absence of Spastic Paralysis, J. Biol. Chem., 1978, 253:125-129.
Jankovic, Botulinum Toxin in Clinical Practice, J. Neurol. Neurosurg. Psychiatry, 2004, 75:951-957.
Janz, et al., SV2A and SV2B Function as Redundant Ca2+ Regulators in Neurotransmitter Release, Neuron, 1999, 24:1003-1016.
Kaplan, Mechanisms of Cellular Iron Acquisition: Another Iron in the Fire, Cell, 2002, 111:603-606.
Kleemann, et al., Cytokines and Atherosclerosis: A Comprehensive Review of Studies in Mice, Cardiovascular Research, 2008, 79:360-376.
Kozaki, et al., Antigenic Structure of Clostridium Botulinum Type B Neurotoxin and its Interaction with Gangliosides, Cerebroside, and Free Fatty Acids, Infection and Immunity, 1987, 55:3051-3056.
Lehtolainen, et al., Targeting of Biotinylated Compounds to Its Target Tissue Using a Low-Density Lipoprotein Receptor-Avidin Fusion Protein, Gene Therapy, 2003, 10:2090-2097.
Mahrhold, et al., The Synaptic Vesicle Protein 2C Mediates the Uptake of Botulinum Neurotoxin A Into Phrenic Nerves, FEBS Letters, 2006, 580:2011-2014.
Meng, et al., Blockade of Tumor Necrosis Factor Alpha Signaling in Tumor-Associated Macrophages as a Radiosensitizing Strategy, Cancer Res., 2010, 70(4):1534-1543.
Mollinedo, et al., Role of Vesicle-Associated Membrane Protein-2, Through Q-Soluble N-Ethylmaleimide-Sensitive Factor Attachment . . . in the Exocytosis of Specific and Tertiary Granules of Human Neutrophils, Journal of Immunology, 2003, 170:1034-1042.
Mosser, et al., Exploring the Full Spectrum of Macrophage Activation, Nat. Rev. Immunol., 2008, 8:958-969.
Moulding, et al., Mcl-1 Expression in Human Neutrophils: Regulation by Cytokines and Correlation with Cell Survival, Blood, 1998, 92:2495-2502.
Murray, et al., A Role for the Phagosome in Cytokine Secretion, Science, 2005, 310:1492-1495.
Rossetto, et al., VAMP/Synaptobrevin Isoforms 1 and 2 are Widely and Differentially Expressed in Nonneuronal Tissues, Journal of Cell Biology, 1996, 132:167-179.
Rummel, et al., Synaptotagmins I and II Act as Nerve Cell Receptors for Botulinum Neurotoxin G., Journal of Biological Chemistry, 2004, 279:30865-30870.
Russo, et al., TNF-alpha as a Promising Therapeutic Target in Chronic Asthma: A Lesson from Rheumatoid Arthritis, Clinical Science, 2005, 109:135-142.
Schiavo, et al., Neurotoxins Affecting Neuroexocytosis, Physiological Review, 2000, 80:717-766.
Stow, et al., SNAREing Immunity: The Role of SNAREs in the Immune System, Nature Reviews Immunology, 2006, 6:919-929.
Yeh, et al., SV2 Mediates Entry of Tetanus Neurotoxin into Central Neurons, PLoS Pathogens, 2010, 6:e1001207, 12 pages.

* cited by examiner

METHOD FOR SELECTIVE TARGETING AND ENTRY OF BACTERIAL TOXINS TO CELLS

CROSS-REFERENCE TO RELATED APPLICATIONS

This application claims the benefit of U.S. Provisional Patent Application No. 61/471,406, filed Apr. 4, 2011, which is incorporated herein by reference in its entirety.

STATEMENT REGARDING FEDERALLY SPONSORED RESEARCH OR DEVELOPMENT

This invention was made with government support under AI057744 awarded by the National Institutes of Health. The government has certain rights in the invention.

FIELD OF THE INVENTION

This invention generally relates to the delivery of therapeutic molecules to cells. In particular, this invention is directed to the selective targeting and entry of bacterial toxins or toxic bioactive fragments thereof to a wide variety of mammalian cell types.

BACKGROUND OF THE INVENTION

The clostridial neurotoxins (CNTs), which include seven botulinum neurotoxin (BoNT) serotypes (A-G) and tetanus neurotoxin (TeNT), have been integral for studying neuro-exocytosis. Intoxication by BoNTs causes flaccid paralysis whereas TeNT causes rigid paralysis. Because of these symptoms, Justinus Kerner envisioned the therapeutic potential of the BoNTs in the 1800s. Finally in 1989, BoNT/A (Botox®, Allergan Inc) and in 2000, BoNT/B (Myobloc™, Elan Pharmaceuticals Inc) were approved for treatment of human patients with facial nerve disorders and cervical dystonia, respectively.

Currently, most, if not all, therapeutic applications of the BoNTs involve the inhibition of neurotransmitter release from neurons. The targets for these toxins are neuronal SNARE proteins. SNAREs, which include syntaxin and SNAP-25 on the target membrane and synaptobrevin on vesicles, form the core of a conserved membrane fusion machine that mediates neuronal exocytosis. However, it is well established that SNARE proteins are ubiquitously expressed and are important for secretion in many other cell types, which include goblet cells in the lung and immune cells including eosinophils, neutrophils, macrophages, and mast cells. Inhibition of secretion from these cells, using CNTs, could revolutionize treatment options for cystic fibrosis (goblet cells), allergy (mast cells), and chronic inflammation (macrophages). However, the lack of toxin receptors naturally protects nonneuronal cells from the CNTs. Thus, the full therapeutic potential of these toxins has not been fulfilled due to their inability to target cells other than neurons.

SUMMARY OF THE INVENTION

In a first aspect, the present invention provides a method for selectively targeting and entry of a bacterial toxin to a cell. Such a method includes the step of contacting a cell with a bacterial toxin or toxic bioactive fragment thereof associated with an antibody or ligand that is specific to a target on the cell. The antibody or ligand selectively binds the target on the cell and the bacterial toxin or fragment thereof is internalized and enters the cell.

In certain embodiments, the bacterial toxin is a *clostridium* neurotoxin or a bioactive toxic fragment thereof. Accordingly, the bacterial toxin may be, e.g., a botulinum neurotoxin A (BoNT/A), botulinum neurotoxin B (BoNT/B), botulinum neurotoxin C (BoNT/C), botulinum neurotoxin D (BoNT/D), botulinum neurotoxin E (BoNT/E), botulinum neurotoxin F (BoNT/F), botulinum neurotoxin G (BoNT/G), tetanus neurotoxin (TeNT), Diptheria toxin, *Pseudomonas* exotoxin, or a bioactive toxic fragment thereof. In particular embodiments, the toxic bioactive fragment of the bacterial toxin lacks a functional receptor binding domain.

The bacterial toxin or toxic bioactive fragment thereof is associated in various embodiments to the antibody or ligand by an avidin/biotin or streptavidin/biotin linkage. Alternatively, the bacterial toxin or toxic bioactive fragment thereof is associated to the antibody or ligand by a covalent chemical linkage. Another linkage option calls for the bacterial toxin or toxic bioactive fragment thereof to be associated to the antibody or ligand via a chimeric polypeptide fusion. The association may also be provided by the antibody or ligand's recognition of and binding to the toxin or toxic bioactive fragment.

The antibody useful in the method is selected from a wide variety of antibodies recognizing targets at or associated with the plasma membrane or secretory vesicle of a selected cell type. Exemplary antibodies, include, but are not limited to, an IL-5 antibody, IgE, a CD64 antibody, a CD25 antibody, a CD11b antibody, a Muc5AC antibody, a Muc2 antibody, a MAC-1/3 antibody, a dopamine transporter antibody, a vesicular dopamine transport antibody, a CD177 antibody, a low density lipoprotein receptor (LDLR) antibody transferring receptor antibody, or an EMA/MUC1 antibody. Likewise, ligands useful in the present methods include entities such as, e.g., IL-5, transferrin, goblet cell antigen, an atoxic lipopolysaccharide, mannosylated toxin, or an RGD peptide. A target plasma membrane protein or a protein located at a plasma membrane of the cell is, in a preferred embodiment, a receptor protein. In certain embodiments, the antibody recognizes the toxin or bioactive fragment and targeting and entry are facilitated by interaction of the antibody's Fc region with one or more components of the cell's complement system.

The present methods exhibit robust utility and are applicable to a wide range of cell types in both the in vitro and in vivo settings, including, e.g., immune cells, neuronal cells, exocrine gland cells, or endocrine gland cells. In certain embodiments, the method targets a cancer or tumor cell.

In a second aspect, the invention encompasses a method for reducing a secretion from a cell. Such a method includes the step of contacting a cell with a bacterial toxin or toxic bioactive fragment thereof associated with an antibody or ligand that is specific to a target on the cell. The antibody or ligand selectively binds the target on the cell and the bacterial toxin or fragment thereof is internalized and enters the cell, whereby a secretion from the cell is reduced.

The secretion reduced by the inventive method is, in certain embodiments, physiologically-associated with asthma, inflammation, allergy, anaphylactic shock, cystic fibrosis, bipolar disorder, Tourette syndrome, epilepsy, cancer, Crohn's disease, rheumatoid arthritis, or acne in a subject.

The invention is further directed to a composition for selectively targeting and facilitating entry of a bacterial toxin to a cell. Such a composition includes a bacterial toxin or toxic bioactive fragment thereof associated with an antibody or ligand that is specific to a target on a cell. The antibody or ligand selectively binds the target on the cell and the bacterial toxin or fragment thereof is thereby internalized and enters the cell.

The bacterial toxin or toxic bioactive fragment thereof is associated in various embodiments to the antibody or ligand by an avidin/biotin or streptavidin/biotin linkage. Alternatively, the bacterial toxin or toxic bioactive fragment thereof is associated to the antibody or ligand by a covalent chemical linkage. Another linkage option calls for the bacterial toxin or toxic bioactive fragment thereof to be associated to the antibody or ligand via chimeric polypeptide fusion. The association may also be provided by the antibody or ligands recognition and binding of the toxin or toxic bioactive fragment thereof.

The antibody useful in the present composition is selected from a wide variety of antibodies having targets at or associated with the plasma membrane or secretory vesicle of a selected cell type. Exemplary antibodies, include, but are not limited to, an IL-5 antibody, IgE, a CD64 antibody, a CD25 antibody, a CD11b antibody, a Muc5AC antibody, a Muc2 antibody, a MAC-1/3 antibody, a dopamine transporter antibody, a vesicular dopamine transport antibody, an LDLR antibody, a transferring receptor antibody, a CD177 antibody or an EMA/MUC1 antibody. Likewise, ligands useful in the present composition include entities such as, e.g., IL-5, transferrin, goblet cell antigen, a toxic lipopolysaccharide, mannosylated toxin, or an RGD peptide. A target plasma membrane protein or a protein located at a plasma membrane of the cell is, in a preferred embodiment, a receptor protein. In certain embodiments, the antibody recognizes the toxin or bioactive fragment and targeting and entry are facilitated by interaction of the antibody's Fc region with one or more components of the cell's complement system.

The present compositions exhibit robust utility and are applicable to selectively targeting and directing entry of bacterial toxins in a wide range of cell types in both the in vitro and in vivo settings, including, e.g., immune cells, neuronal cells, exocrine gland cells, or endocrine gland cells. In certain embodiments, the composition is capable of targeting a cancer or tumor cell.

In yet another aspect, the invention is directed to a kit for providing selective targeting and entry of a bacterial toxin or toxic bioactive fragment thereof to a cell. Such a kit includes a composition described and claimed herein and an instructional material.

The invention also contemplates the use of a composition described and claimed herein for the manufacture of a medicament for the selective targeting and entry of a bacterial toxin or a toxic bioactive fragment thereof to a cell in a subject. As well, the invention includes the use of a composition as described and claimed herein for the manufacture of a medicament for reducing a secretion from a cell in a subject.

The presently-described and claimed compounds and methods provide various advantages over prior compositions and methods in that they provide for the selective targeting and entry of a wide variety of bacterial toxins to cell types beyond the neuronal cell types normally-targeted by these toxins.

Other objects, features and advantages of the present invention will become apparent after review of the specification, claims and drawings.

BRIEF DESCRIPTION OF THE DRAWINGS

FIG. 1: Functional entry of biotin-CNTs into fibroblasts that express a chimeric receptor. (a) Schematic of the AvLDL chimeric receptor. A GFP was fused to the C-terminal intracellular end of the LDLR TMD (aa 788-861) and monomeric avidin was fused to the extracellular N-terminus. (b) Model of the experimental protocol. HEK-293 cells were transfected with the AvLDLR chimera, the appropriate SNARE, and then incubated with biotin-CNTs. Avidin binds the biotin-CNTs and the complex is internalized into endosomes, where the acidic environment induces translocation of the L chain into the cytosol where it cleaves SNAREs. (c) HEK-293 cells expressing the chimeric receptor and the appropriate SNARE target for each CNT were lysed and subjected to immunoblot analysis after treatment with the toxins. Biotin-BoNT/A and biotin-BoNT/E were able to enter HEK-293 cells expressing AvLDLR and cleave 81% and 54% of SNAP-25, respectively. The arrows denote full-length (f) and the cleaved (c) form of SNAP-25. Cell lysates were probed for β-actin as a loading control. (d) Biotin-TeNT, biotin-BoNT/F, and biotin-BoNT/B behaved similarly and were able to enter and cleave 84%, 54% and 61% of syb II in cells expressing AvLDL, respectively. HEK-293 cells that expressed a control vector were resistant to the action of the CNTs

FIG. 3: Retargeted BoNT/B reduces TNFα secretion from primary human BMDMs. (a) TNFα release from human BMDMs was monitored by ELISA. When 6 nM BoNT/B was preincubated with the αB, we observed a 45% decrease in the release of TNFα. Antibody and BoNT/B alone conditions were not significantly different from control. Error bars represent SEM, n=7, p≤0.01. (b) MTS assay indicating no significant decrease in metabolic activity in response to the indicated treatments as compared to control (n=5). (c) Dose response of retargeted BoNT/B on TNFα release from human BMDMs. The concentrations indicated are for BoNT/B, which was preincubated with αB. Error bars represent SEM, n≥3, $R^2$=0.65 $IC_{50}$=6.1 nM. (d) ELISA of matrix metalloprotease-9 (MMP-9) release; secretion was not inhibited by retargeted BoNT/B. Error bars represent SEM, n≥3. (e) MTS assay indicating no decrease in metabolic activity upon titration of BoNT/B. Error bars represent SEM, n≥3. (f) TNFα release from allergic asthmatic patients was reduced by 50% when treated with retargeted BoNT/B (6 nM). Error bars represent SEM, n=6, p≤0.01. (g) Human BMDMs from allergic patients with no diagnosis of asthma exhibited a 39% reduction in TNFα secretion when incubated with 6 nM retargeted BoNT/B. Error bars represent SEM, n=5, **p≤0.01.

FIG. 5: BoNT/F reduces EPO release in primary human eosinophils. a) Human primary eosinophils were incubated in media with the addition of PBS (control), 3 μg of biotinylated CD11b antibody (ab), biotinylated BoNT/F (75 nM) with CD11b antibody (ab+BoNT/F pre-incubated with avidin and biotinylated CD11b antibody (avidin+ab+BoNT/F). Cells were incubated at 37° C. for 24 hrs. Eosinophil peroxidase (EPO) release was analyzed using a peroxidase assay in the absence of presence of ionomycin stimulation. We observed a decrease in ionomycin-induced EPO release in the presence of the pre-conjugated complex (avidin+ab+BoNT/F) as compared to control.

DETAILED DESCRIPTION OF THE INVENTION

I. In General

Figure 2:
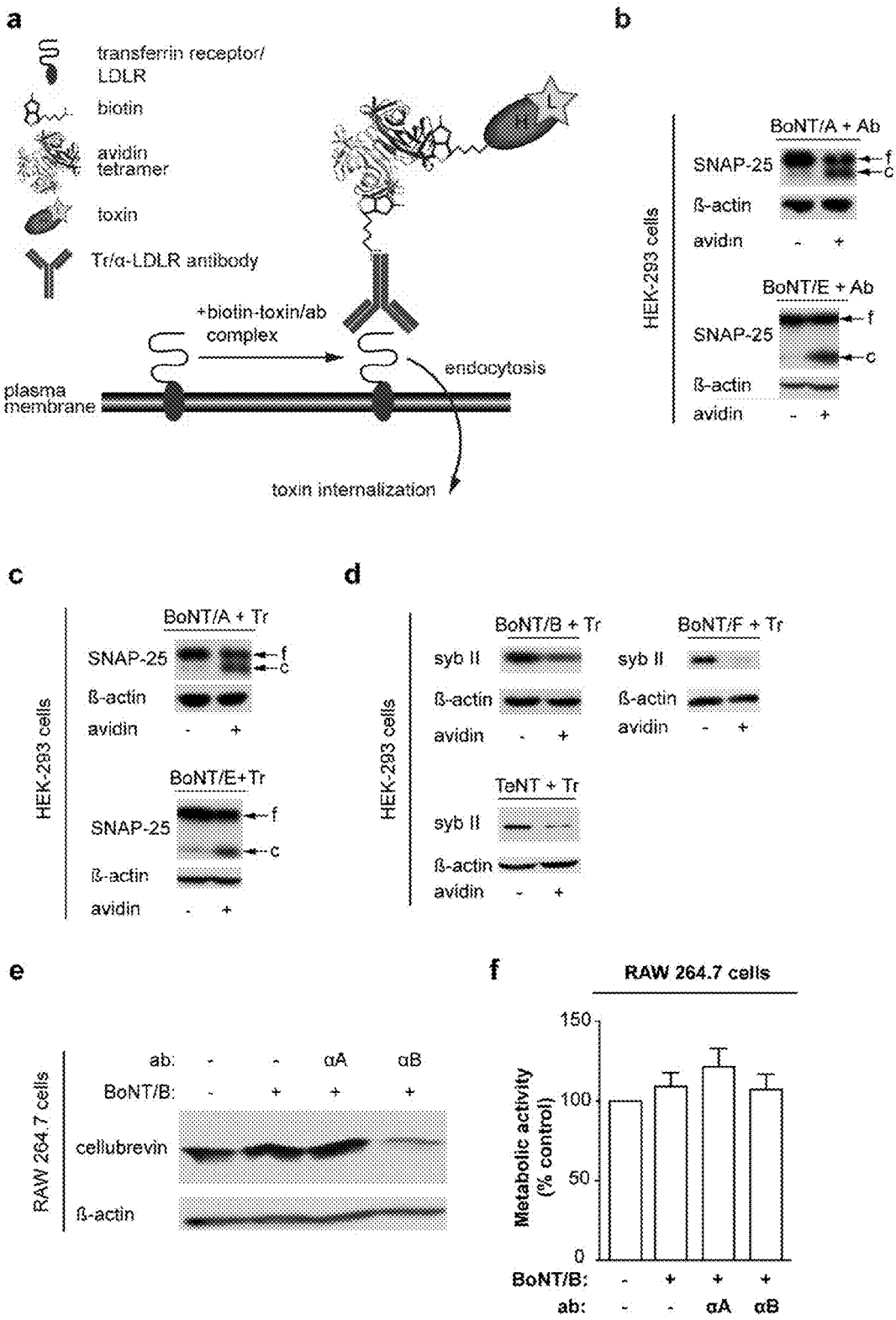
FIG. 2: CNTs, linked to an antibody or Tr, enter nonneuronal cells without expression of chimeric receptors. (a) Model of the experimental protocol. The biotin-toxin is attached to avidin and in turn attached to a biotin-antibody or biotin-Tr. Tr, or the antibody, mediate binding to native cell surface proteins and internalization via endocytosis. Functional entry of the toxin into the cytosol was monitored by cleavage of exogenously introduced SNAREs. (b) Immunoblots showing that both biotin-BoNT/A and biotin-BoNT/E, when linked to an antibody directed against the extracellular domain of the LDLR, cleaved 45% of SNAP-25 in HEK-293 cells. The arrows denote full-length (f) and the cleaved (c) form of SNAP-25. Cell lysates were probed for β-actin as a loading control. (c) When linked to biotin-Tr with avidin, biotin-BoNT/A and biotin-BoNT/E cleaved 46% and 33% of SNAP-25, respectively. (d) Similarly, biotin-BoNT/B, biotin-TeNT, and biotin-BoNT/F, when attached to Tr through avidin, cleaved 28%, 74%, and 89% of syb II, respectively. (e) BoNT/B, which had been preincubated with αB, cleaved 68% of ceb in RAW264.7 cells. Ceb levels were unaffected in cells incubated with BoNT/B alone or BoNT/B incubated with a BoNT/A specific antibody (αA). (1) MTS assay indicating no significant decrease in metabolic activity in response to toxin treatment as compared to control. Error bars represent SEM, n=3.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by claims contained in this or any later-filed nonprovisional application.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

II. The Invention

The entry and action of bacterial toxins on target cells require the presence of specific molecules, which act as toxin receptors, on the surface of target/host cells. This requirement for "native receptors" thus limits the potential for therapeutic effects on other kinds of target cells. For instance, botulinum neurotoxin serotype B (BoNT/B) targets neurons, but it has potential applications for reducing the release of cytokines and other pro-inflammatory agents from immune cells such as neutrophils and eosinophils. Unfortunately, BoNT/B cannot enter immune cells, which lack the naturally occurring toxin receptor molecules. Accordingly, there is considerable interest in finding ways to target the botulinum neurotoxins to cell types other than neurons, above and beyond cells in the immune system; these include driving toxin entry into goblet cells to shut down mucus secretion in cystic fibrosis patients and any other disease that is associated with hyper secretion or the secretion of unwanted factors.

To address the inability of bacterial toxins, such as the botulinum and tetanus neurotoxins, to enter a target cell to treat a wider range of diseases, the present inventors have developed a generalized approach to direct toxin entry into new target cells for potential therapeutic purposes. In one embodiment, this directed approach utilizes biotin-avidin/streptavidin interactions and can be potentially generalized to a wide range of toxin molecules in addition to the botulinum and tetanus toxins.

To further illustrate their approach, the inventors have demonstrated that chemically biotinylated toxins can be made to enter new kinds of target cells through the expression of a low-density lipoprotein receptor (LDLR)-avidin (monomeric) chimera in the target cell. They have tested this exemplary chimera using HEK-293 (human embryonic kidney) cells which do not express the natural protein receptors for the clostridial neurotoxins. The inventors have shown that by expressing the chimeric receptor in these cells, all of the toxins tested (BoNT/A, B, E, F and tetanus toxins) were able to gain entry and to cleave their substrate SNARE proteins (SNAREs form the core of the membrane fusion apparatus in cells; these toxins block secretion by cleaving SNAREs). These experiments demonstrate that the toxins can selectively enter and block secretion in cells types that are distinct from their natural targets, neurons.

To further improve the present targeting strategy, the toxin has been altered so that it is no longer able to enter its normal target cells (again, neurons) such that neurological side effects can be avoided. This alteration may be achieved, e.g., by replacing the receptor-binding domain of each toxin with a biotin acceptor peptide that is used to specifically biotinylate the toxin. This results in a toxin that will be non-toxic in vivo, but will have its intended action on cells expressing the avidin chimeric receptor. Chimeric receptors can also include combinations of LDLR, transferrin receptor, other recycling plasma membrane proteins, avidin, and streptavidin.

The chimeric receptor approach detailed above demonstrates that the inventors can target toxins without their natural receptor and without knowledge of the identity of the receptor protein (as in the case of BoNT/F, for which the receptor is not known). To expand the therapeutic capabilities of the toxins, the inventors further developed a strategy to drive toxin entry into novel target cells which does not require the expression of chimeric receptors or a gene therapy approach. This technique, termed the "sandwich method", involves three components and is illustrated by a moiety made up of a biotinylated toxin, a biotinylated antibody (or ligand for a novel, naturally occurring receptor), and an avidin/streptavidin linkage between them. Since avidin/streptavidin is naturally a tetramer, it can bind a maximum of four biotinylated molecules at the same time. In effect, the biotinylated toxin hitchhikes on the biotinylated antibody's (or ligand's) ability to enter cells in order to exert its function, through their linkage through avidin/streptavidin. This method does not require gene therapy and the potential for applications is virtually limitless.

The inventors demonstrate herein that the clostridial neurotoxins do not need their natural receptors to function and since tetanus and clostridial neurotoxins are "AB toxins", any potential toxin in the AB toxin family can be used. Thus, a variety of toxin effects can be harnessed and used for therapy. AB toxins are a large family of bacteria toxins that contain two domains: domain A is an enzymatic domain and domain B is the receptor-binding domain. Thus, the toxin component in the sandwich method can have a range of effects from reducing secretion with the clostridial neurotoxins to causing cell death with *pseudomonas* exotoxin.

Another significant advantage of the sandwich method includes a large degree of flexibility to target the toxins to a wide range of cells with the nearly infinite choices of receptor ligands and antibodies available. Ligands such as transferrin, which helps transport iron into cells, and antibodies directed against the extracellular domain of the LDL-receptor, which is expressed in virtually all cells, can be used to target the toxins to virtually any cell type. In contrast, antibodies specific for glutamatergic neurons and receptor ligands such as IL-5, which is specific for eosinophils can direct the toxins to specific cell types for various diseases. This system is also highly modular, and the placement of avidin/streptavidin and biotin between all molecules can be interchanged. Recombinant toxins with the receptor-binding domain replaced with an antibody (or ligand)—either by fusing cDNA or via chemical linkage can be readily generated.

Another embodiment of the invention utilizes an antibody that recognizes and binds a toxin or toxic bioactive fragment thereof and is subsequently targeted to and internalized via the antibody's Fc region interacting with one or more component of the cell's complement system. Linkage between the toxin or fragment thereof and the antibody is thereby provided by a cellular mechanism present in a variety of immune cell types.

As can be appreciated, the present invention provides the opportunity to direct toxin to target cells other than neurons, e.g., macrophages. Macrophages are key players in diseases such as sepsis, atherosclerosis, Crohn's disease, and rheumatoid arthritis. Macrophages secrete a potent pro-inflammatory cytokine, TNFα, which plays a role in many diseases such as rheumatoid arthritis, ankylosing spondylitis, Crohn's disease, psoriasis, hidradenitis suppurativa and refractory asthma.

Using the inventors' newly developed targeting strategy, it is possible to inject the toxin complex at the site of inflammation, to prevent local secretion of TNFα, while circumventing potential side effects from global TNFα decrease. In addition, the approved TNFα inhibitors are typically injected every other week. With the lifespan of macrophages on the order months, it seems likely that the prolonged effects of BoNT/B, could reduce the frequency of injections. One of the crippling side effects of the immunotoxins has been unwanted toxicity; however, with the exception of BoNT/C, none of the CNTs cause cell death. Furthermore, the CNTs are on the order of a million times less potent without their HC.

In another embodiment, the present invention provides tools to examine the role of SNAREs in organelle targeting and the release of cytokines in primary immune cells. The clostridial neurotoxins have proved to be an invaluable tool in the study of neuroexocytosis and the critical role which SNAREs play in membrane fusion. Neurons have the natural ability to take up the toxins; however, primary human immune cells do not express the native receptors for these toxins and also are very resistant to transfection and infections techniques to modify protein expression levels. To study the SNARE mediated secretion of cytokines in immune cells, the cells generally have to be permeabilized to allow the activated L chain of the toxin to enter the cell and cleave the SNAREs. However, such nonphysiological treatment of these cells generally reduces the viability of the cell. Other experiments rely on the use of cell lines that mimic the intended immune cell; however, where the cell lines are an exact model system is questionable. Accordingly, the targeting technique disclosed herein brings into the immunology field a new tool that can be used to determine which SNAREs are important for release of cytokines. While similar techniques to specifically target macrophages can be used, conjugating the toxins to transferrin and also antibodies directed against the LDL receptor can allow the toxins to enter almost any cell type.

Additional embodiments of the present invention are envisioned to be applicable in treating a wide range of diseases. Specific applications include, but are not limited to, use of a BoNT/B-IL5 complex to target BoNT/B to eosinophils to reduce the release of cytokines and proinflammatory agents during acute asthma.

As well, goblet cells release mucus which is an important player during cystic fibrosis (CF), a devastating disease with limited treatment options. Many CF patients have complications with excess mucus in their lungs and require the use of a nebulizer to help clear their lungs. To improve their quality of life, one could use, per the present invention, a MUC5AC antibody linked to BoNT/C to reduce release of mucus from goblet cells and improve their respiratory function.

Furthermore, the present invention would facilitate diphtheria toxin, which causes cell death, to be linked to cyclic RGD peptides for binding cancer cells to specifically cause cancer cell death with little to no cell death in healthy tissue.

In yet another embodiment, the invention provides for customizing a therapeutic effect by targeting the toxins to either a plasma membrane protein or a protein located on a secretory vesicle. For example, if a group of inhibitory neurons are too active, the inventors can target a toxin to a plasma membrane protein specifically expressed on the surface (at least transiently) of these neurons to drive entry in an activity independent manner (normally most of the toxins require activity to enter neurons). This approach will have a large reduction of inhibitory transmission of the entire population of inhibitory neurons. However, if the inventors wish to specifically target the top fraction of neurons in terms of activity in that area, they can target the toxin to a synaptic vesicle membrane protein; more active neurons will internalize a larger amount of the toxin relative to their quiescent peers. This will silence the overactive inhibitory neurons, but would allow normal signaling for other less active inhibitory neurons in the population. Thus the targeting method described here is potentially ideally suited for fine-tuning the general effects and actions of the toxins.

Tables 1 and 2 below provide further description of exemplary therapeutic entities which demonstrate the medical utility of the inventive approach disclosed herein.

TABLE 1

Targeting strategies for specific cells types and associated diseases.

| toxin/function | target cell | antibody/receptor ligand | applicable disease |
| --- | --- | --- | --- |
| BoNT/B, D, F, G, TeNT Reduced secretion | eosinophils, | IL-5, IL-5 antibody, IgE | asthma |
| BoNT/B, D, F, G, TeNT Reduced secretion | neutrophils | CD64 antibody | inflammation |
| BoNT/C Reduced secretion | mast cells | CD25 antibody | allergies, anaphylactic shock |
| BoNT/C Reduced secretion | goblet cells | Muc5AC antibody Muc2 antibody | cystic fibrosis |
| BoNT/A-G, TeNT Reduced secretion | dopaminergic neurons | dopamine transporter antibody | bipolar disorder tourrette syndrome |
| BoNT/A-G, TeNT Reduced secretion | glutamatergic neurons | vesicular dopamine transporter antibody | epilepsy |
| Diptheria toxin/*Pseudomonas* exotoxin Cell death | cancer cells/tumor cells | RGB peptides | cancer |
| BoNT/A-G, TeNT Reduced secretion | sebaceous glands | antibodies against (EMA)/MUC1 | acne |

TABLE 2

Additional targeting strategies for specific cell types and associated diseases.

| Primary Cell | Secreted Substance(s) | Associated SNAREs | Cell Line(s) | Toxin | Targeting strategy | Assoc. Disease |
| --- | --- | --- | --- | --- | --- | --- |
| Macrophages | TNFα | ceb | RAW264.7 | ceb: BoNT/B | Atoxic LPS, mannosylated toxin, MAC-1/3 antibody | Inflammation, alherosclerosis, cancer |
| Mast Cells | Histamine | STX3 | RBL-2H3 | STX3: BoNT/C | IgE | Allergies, anaphylatic shock |
| Goblet Cells | Mucin | STX2/3 | HT29-MTX, LS174T | STX2/3: BoNT/C | Goblet cell antigen | Cystic fibrosis |
| Neutrophils | Defensins, cathepsins, gelatinase, (to be screened) | SNAP-25, syb I/II | HL-60S | SNAP-25: BoNT/A + E syb I/II: BoNT/B | CD177 antibody | Inflammation |
| Eosinophils | Eosinophil peroxidase, eosinophil cationic protein, (to be screened) | syb II | HL-60s clone 15 | syb II: BoNT/B | IL-5 | Asthma |

Additional embodiments of the present invention are envisioned to be applicable in reducing a secretion from a cell. Specific applications can include, without limitation, use of a BoNT/B-IL5 complex to target BoNT/B to eosinophils to reduce secretion of cytokines and proinflammatory agents during acute asthma. In some cases, secretion of cytokines and proinflammatory agents such as TNFα is reduced. In other embodiments, a secretion can be mucus, mucin, histamine, eosinophil peroxidase (EPO), a defensin, a cathepsin, gelatinase, eosinophil cationic protein, or any other secreted agent.

The present methodology provides a large degree of flexibility to target toxins to a wide range of cells with the nearly infinite choices of receptor ligands and available antibodies. In this regard, ligands such as transferrin, which helps transport iron into cells, and antibodies directed against the extracellular domain of the LDL-receptor, which is expressed in virtually all cells, can be used to target the toxins to virtually any cell type. In contrast, antibodies specific for glutamatergic neurons and receptor ligands such as IL-5, which is specific for eosinophils can direct the toxins to specific cell types for the treatment of various diseases. Accordingly, the present methodology is also highly modular, and the selection of components is highly interchangeable. For example, an avidin/streptavidin and biotin linkage can be interchanged by resort to recombinant toxins with the receptor-binding domain replaced with an antibody (or ligand)—either by fusing cDNA or via chemical linkage. In certain embodiments, the antibody recognizes the toxin or bioactive fragment and targeting and entry are facilitated by interaction of the antibody's Fc region with one or more components of the cell's complement system.

Various exemplary embodiments of compositions and methods according to this invention are now described in the following examples. The following examples are offered for illustrative purposes only and are not intended to limit the scope of the present invention in any way. Indeed, various modifications of the invention in addition to those shown and described herein will become apparent to those skilled in the art from the foregoing description and the following examples and fall within the scope of the appended claims.

III. Examples

Example 1

Retargeting Clostridial Neurotoxins to Macrophages Reduces TNFα Release

Botulinum neurotoxin (BoNT) A and B are used therapeutically to treat a broad range of neuropathic disorders by cleaving SNARE (soluble NSF [N-ethylmaleimide sensitive factor] attachment protein receptors) proteins to inhibit membrane fusion and neurotransmitter release from neurons. However, both toxins have untapped potential for therapy and for studying the role of SNAREs in nonneuronal cells. Here we describe novel methods to retarget BoNT/A, BoNT/B, and other members of the clostridial neurotoxin (CNT) family, to nonneuronal cells that lack receptors for these toxins, thereby broadening their uses to treat disease. One potential target is macrophages, which mediate inflammation and are involved in many chronic diseases. Retargeted BoNT/B successfully cleaved cellubrevin (ceb), which mediates the release of tumor necrosis factor-α (TNFα), in a murine macrophage cell line (RAW264.7). We extended these experiments to primary human blood monocyte-derived macrophages (BMDMs) and observed a significant reduction in interferon-γ and lipopolysaccharide (IFNγ/LPS) induced release of TNFα. BoNT/B, lacking its receptor binding domain (BoNT/BΔHC), retained its ability to suppress stimulated TNFα release from human BMDMs, but was ineffective on hippocampal neurons. Finally, mice injected with engineered BoNT/B exhibited a decrease in macrophage recruitment. Thus, retargeted BoNT/B provides a potential therapeutic to inhibit the release of TNFα to potentially combat chronic inflammatory disorders, tumor growth, and the progression of atherosclerosis.

In order to target the toxins to nonneuronal cells, it was important to first investigate whether they were functionally active in the absence of their native receptors. To address this, a new approach was developed to retarget the CNTs to HEK-293 cells, a human embryonic kidney cell line. HEK-293 cells are an ideal model system, due to their lack of native toxin receptors, to study alternative entry methods for the toxins. We note that most of the CNTs enter neurons via recycling synaptic vesicles and where acidification triggers the translocation of toxin molecules into the cytosol where they cleave SNAREs. Therefore, to retarget the toxins to HEK-293 cells, which lack synaptic vesicles, they must be directed to a specific vesicular compartment that is more commonly found in nonneuronal cell types.

Figure 1:
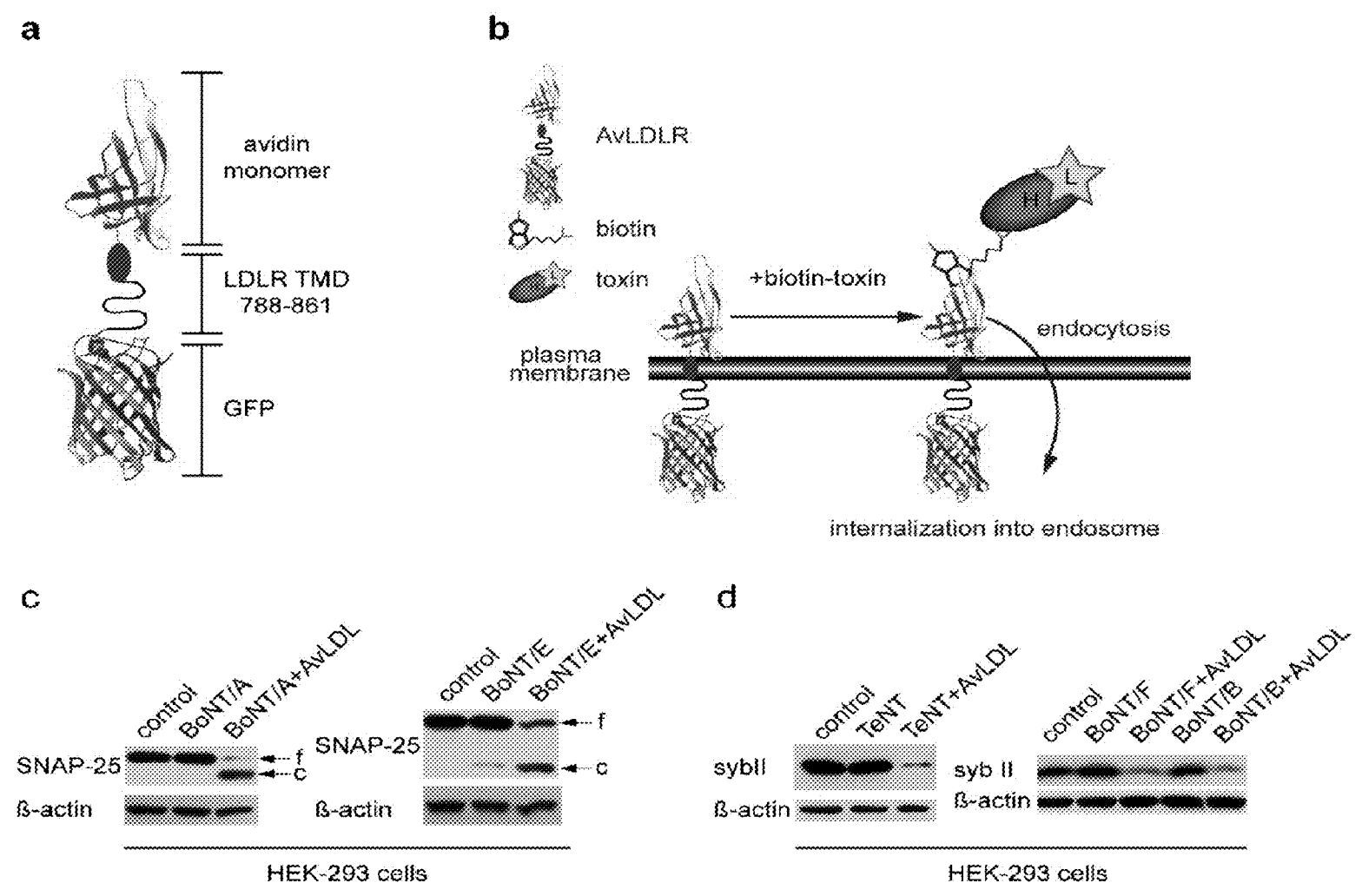

Previously, it has been shown that a chimeric protein containing a fragment of SV2A, the receptor for BoNT/A, BoNT/E, and TeNT, fused to the transmembrane domain (TMD) of the low-density lipoprotein receptor (LDLR) mediated entry of BoNT/E into neurons in the absence of the native receptor. Additionally, it was reported that an avidin monomer-LDLR chimera was capable of binding biotinylated transferrin in vitro and in vivo. Our strategy to redirect the CNTs was to utilize the LDLR which is recycled through endosomes in virtually all cell types. We began by creating an avidin monomer-LDLR (AvLDLR) construct that was tagged with green fluorescent protein (GFP) (FIG. 1a). Next, the CNTs were chemically biotinylated and incubated with HEK-293 cells with or without expression of AvLDLR (FIG. 1b). HEK-293 cells that were transfected with AvLDLR exhibited robust entry of several CNTs, as evidenced by significant cleavage of exogenously-introduced SNAP-25 by biotinylated BoNT/A (biotin-BoNT/A) and biotin-BoNT/E (FIG. 1c), and cleavage of transfected synaptobrevin II (syb II) by biotin-BoNT/B, biotin-BoNT/F, and biotin-TeNT (FIG. 1d). Collectively, these results clearly demonstrate that the CNTs are active when retargeted to an alternative organelle lacking native toxin receptors. Furthermore, CNTs with unidentified receptors, such as BoNT/F, can also be retargeted using this approach.

The fact that many primary cells are resistant to genetic modification or simply do not survive long enough to express chimeric receptors, makes it difficult to study the function of SNAREs in these cells. In order to overcome this obstacle, we used avidin to tether biotin-toxin to biotin-transferrin (Tr) or to a biotin-antibody directed against the extracellular domain of the LDLR, both of which have been reported to be internalized via recycling endosomes in many cell types. We postulated that the toxin complex would be targeted to recycling endosomes via interactions with the Tr receptor or the LDLR (FIG. 2a). Indeed, only when biotin-BoNT/A or biotin-BoNT/E was linked to the antibody or Tr through avidin was there significant cleavage of SNAP-25 that had been expressed in these cells by transfection (FIG. 2b-c). In addition, when biotin-BoNT/B, biotin-BoNT/F or biotin-TeNT was attached to Tr, the toxins were able to enter cells and cleave their substrate, syb II (FIG. 2d). The modular design of the biotin-avidin approach allows tethering of the CNTs to a wide variety of natural ligands or antibodies to study the function of SNAREs in nonneuronal cells that are resistant to the introduction of these toxins through molecular biology approaches. Additionally, when compared to the AvLDLR approach, which tethers the toxin adjacent to the membrane, the antibody-ligand experiments indicate that the significant distance from the membrane, due to the large size of the antibody and tetrameric avidin, did not abrogate the activity of the CNTs.

The data so far indicate that the toxins can function in the absence of their native receptors, in a noneuronal cell line, via a non-synaptic vesicle entry pathway. The next goal was to determine whether these toxins could be retargeted to macrophages, which are important phagocytes and antigen-presenting cells that play key roles in both innate and adaptive immunity. In addition to their ability to phagocytose and degrade microbes, these leukocytes also release a variety of cytokines that regulate inflammation, wound healing, tissue remodeling, and the recruitment of other immune cells. Clinically, tissue macrophages have been linked to a variety of diseases, including sepsis, atherosclerosis, cancer, and chronic inflammatory disorders including rheumatoid arthritis and Crohn's disease. In particular, the secretion of TNFα, a potent pro-inflammatory cytokine secreted primarily by macrophages and monocytes, is thought to play a critical role in many of these diseases.

A recent report demonstrated that in RAW264.7 cells, the delivery of TNFα to the cell surface in response to IFNγ/LPS stimulation was impaired when a substrate of BoNT/B, ceb, was knocked down using siRNA. Ceb is a member of the synaptobrevin family of vesicular SNAREs. To determine if BoNT/B could be specifically retargeted to RAW264.7 cells and cleave ceb, we modified the antibody-mediated delivery method and targeted the toxin to the Fc and complement receptor-mediated endocytosis pathway. Cells were incubated with BoNT/B alone, BoNT/B with an anti-BoNT/A antibody (αA), and BoNT/B with an anti-BoNT/B antibody (αB). In the BoNT/B plus αB condition, the toxin was able to enter cells and cleave ceb (FIG. 2e). Ceb levels in the RAW264.7 cells were unaffected by BoNT/B alone or BoNT/B with αA. None of these treatments significantly affected cell viability as determined by an MTS cytotoxicity assay (FIG. 2f).

To determine the potential of retargeted BoNT/B on a clinical target, we measured the effect of the toxin on TNFα release from human BMDMs. Human BMDMs were treated with BoNT/B, αB alone, and BoNT/B plus αB. Cells treated with BoNT/B, in conjunction with αB, exhibited a ~50% decrease in IFNγ/LPS-induced TNFα release, without significantly affecting cell viability (FIG. 3a-b).

Figure 3:
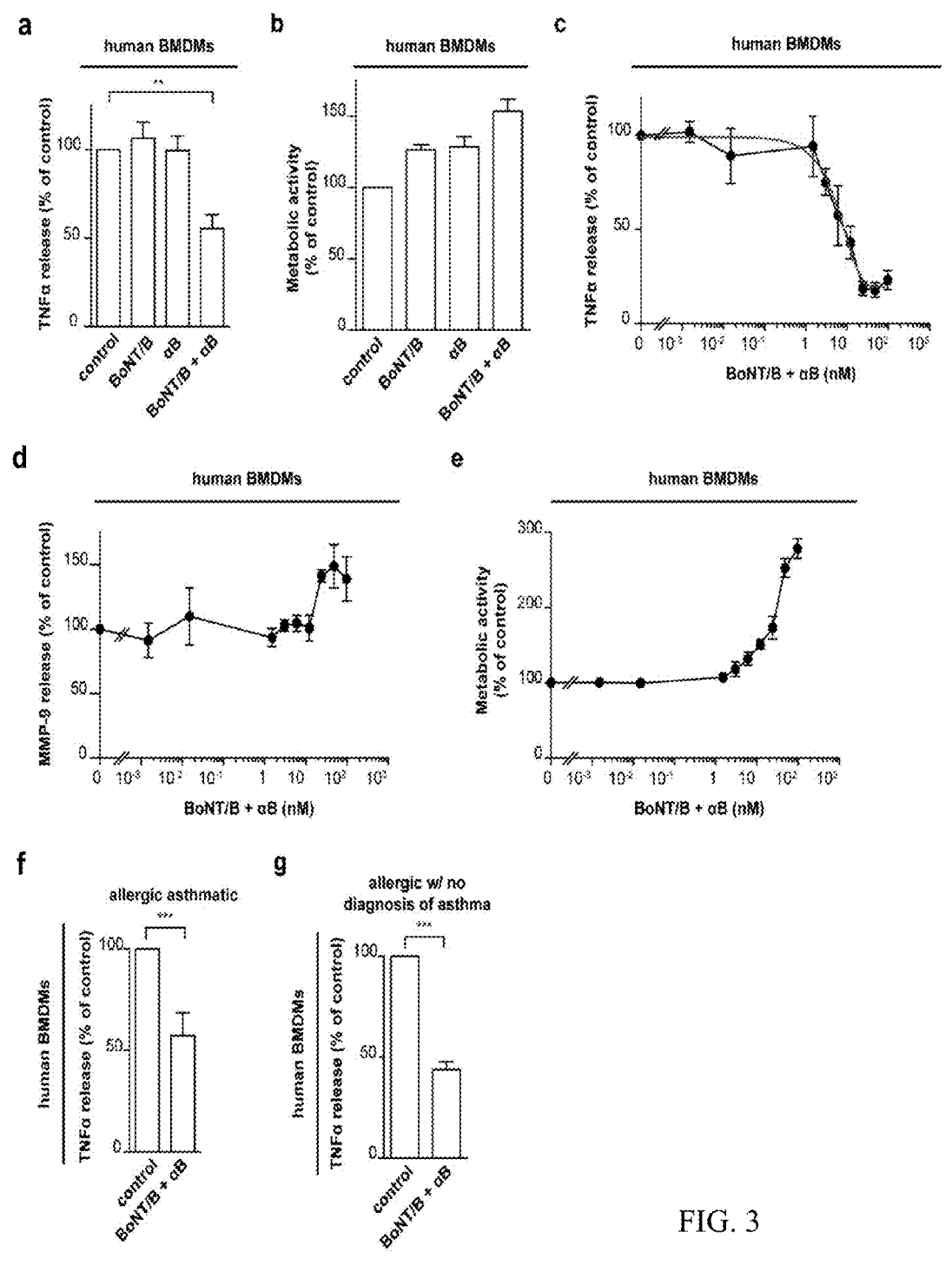

A dose response revealed that the $IC_{50}$ of retargeted BoNT/B on TNFα release was ~6 nM (FIG. 3c). This effect was specific; the release of matrix metalloproteinase-9 (MMP-9), monitored as a control, was not reduced by the retargeted toxin, demonstrating that this enzyme is secreted through a distinct, BoNT/B-insensitive pathway (FIG. 3d). Furthermore, the decrease in TNFα release was not associated with cytotoxicity (FIG. 3e). We note that the increases in metabolic activity at higher doses of retargeted toxin might potentially explain the concomitant increase in MMP-9 release at this concentration range. We note that the donor pool mainly consisted of two groups: clinically-diagnosed allergic asthmatics and allergic patients without asthma. Human BMDMs from both groups exhibited significant decreases in TNFα release in response to IFNγ/LPS, indicating that the retargeted toxin is effective regardless of the asthma/allergy phenotype (FIG. 3f-g).

The antibody-mediated delivery method illustrates the effectiveness in retargeting BoNT/B to human BMDMs; however, use of the intact toxin can potentially result in the intoxication of neuronal cells. Therefore, further experiments were performed utilizing a truncated toxin, BoNT/BΔHC, that lacks its HC domain. The HC domain is the neurospecific binding region that mediates interactions with native receptors on neurons. Upon removal of the HC domain, TeNT becomes ~2.5 million times less toxic. Similar results were found with BoNT/A lacking its HC domain; the truncated toxin was 20 million times less toxic than the intact holotoxin. In principle, BoNT/BΔHC could be retargeted to macrophages without affecting neurons, avoiding potential side effects, but whether the truncated toxin will be able to affect nonneuronal cells is unknown and is addressed below.

Figure 4:
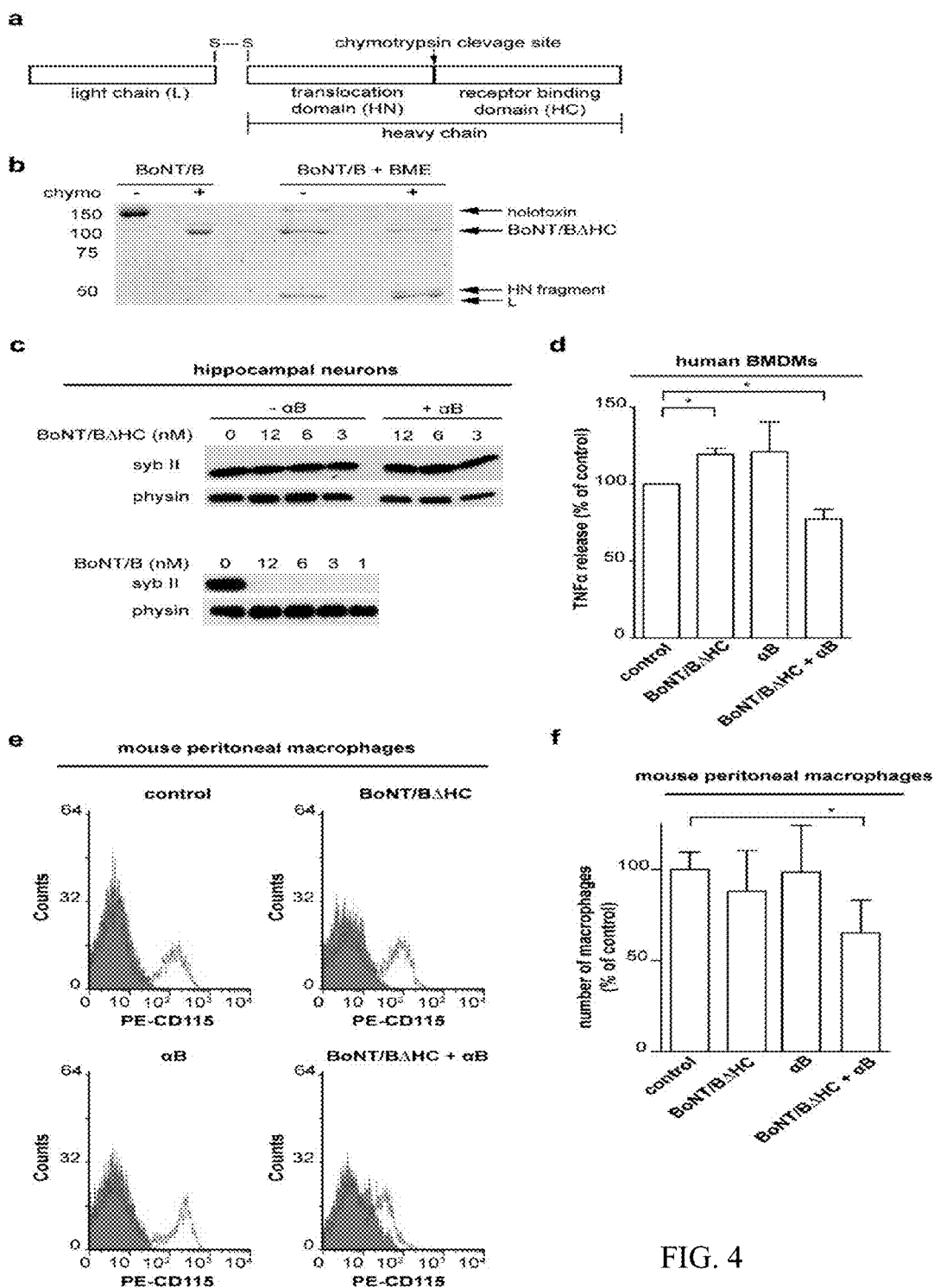
FIG. 4: Retargeting of BoNT/BΔHC to macrophages; injection into mice reduces macrophage recruitment in vivo. (a) Schematic of the structure of BoNT/B with the indicated chymotrypsin hyper-sensitive site between the HC and FlN domains. (b) SDS-PAGE gel of untreated and chymotrypsin-treated BoNT/B stained with Coomassie blue. Full-length holotoxin migrates at 150 kDa while the chymotrypsin fragment (BoNT/BΔHC) migrates at 113 kDa. The smaller chymotrypsin fragment was not detected, probably due to further proteolytic degradation. The disulfide bond in the holotoxin was reduced by β-mercaptoethanol (BME) into 100 kDa and 50 kDa fragments, corresponding to the heavy chain and L chain, respectively. The chymotrypsin fragment was reduced to ~54 and ~59 kDa fragments that correspond to the L chain and the HN domain, respectively. (c) Treatment of hippocampal neurons with BoNT/BΔHC, with and without αB, did not result in cleavage of syb II as compared to BoNT/B holotoxin. Cell lysates were probed for synaptophysin (physin) as a loading control. (d) TNFα release was assessed after treatment with BoNT/BΔHC (1 nM) plus αB and was reduced by 23% as compared to control. Error bars represent SEM, n=3, *p≤0.05. (e) FACS analysis of intraperitoneal cells, isolated from mice injected with indicated agents, exhibited a significant decrease in the CD-115-positive macrophage population (red line) in the BoNT/BΔHC plus αB condition. Cells incubated with a control antibody are represented by the dark gray area. (f) Mice injected with a mixture of BoNT/BΔHC and αB exhibited a ~35% decrease in macrophage recruitment, while either protein alone exhibited no decrease compared to control. Error bars represent SEM, n≥8, *p≤0.05.

In order to produce BoNT/BΔHC, we took advantage of a hyper-sensitive chymotrypsin site that lies between the translocation (HN) and HC domain of the protein (FIG. 4a). Toxin that was treated with chymotrypsin resulted in a ~113 kDa fragment, which could be reduced by β-mercaptoethanol (BME) into two fragments ~59 and ~54 kDa (FIG. 4b). These two fragments correspond to the HN domain and L chain of BoNT/B that are normally held together by a disulfide bond. Further evidence that this fragment does not contain the HC domain comes from the observation that it does not bind gangliosides, a co-receptor for most of the CNTs.

To further confirm the removal of the neurospecific binding domain, we tested whether BoNT/BΔHC could enter and intoxicate neurons by performing a titration of holotoxin and BoNTBΔHC, incubated with and without αB, on cultured hippocampal neurons. Even at concentrations up to 12 nM, BoNT/BΔHC had no detectable activity as demonstrated by the lack of syb II cleavage (FIG. 4c). Thus, BoNT/BΔHC, preincubated with antibody, is not targeted to neurons.

Next, primary human BMDMs were incubated with BoNT/BΔHC in the presence or absence of αB and assayed for TNFα release in response to IFNγ/LPS stimulation. Treatment with BoNT/BΔHC and αB resulted in a ~25% decrease in TNFα release (FIG. 4d), indicating that the HC domain is dispensable for targeted entry into human BMDMs. There was no detectable cytotoxicity from these treatments (data not shown). Finally, when BoNT/BΔHC and αB were administrated in mice with thioglycollate-induced inflammation, FACS (fluorescence activated cell sorting) analysis revealed a ~35% decrease in macrophage recruitment as compared to control, implicating an overall reduced state of inflammation (FIG. 4e-f). These data further confirm that the BoNT/BΔHC is effective at suppressing selective inflammatory responses both in vitro and in vivo.

Figure 6:
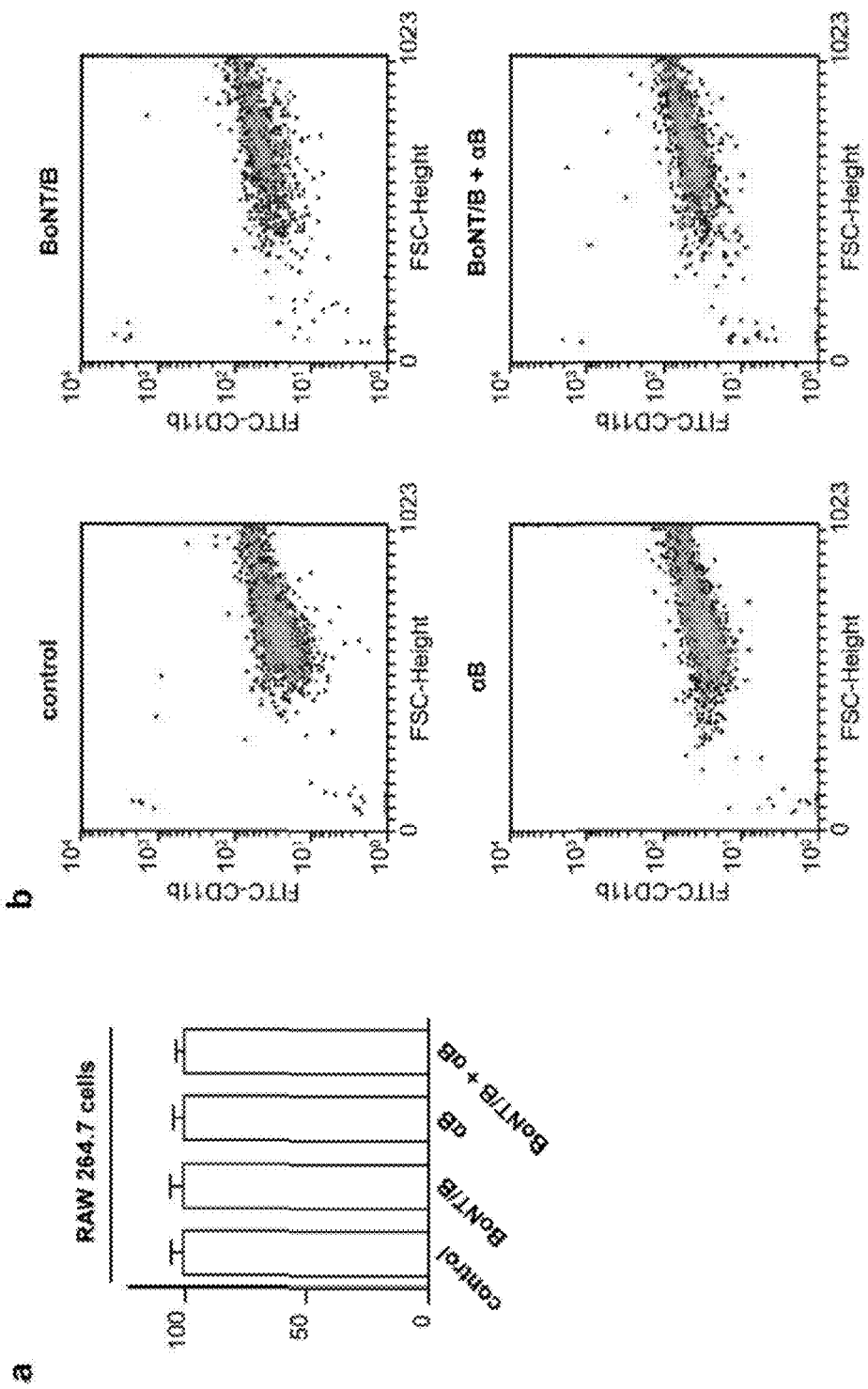
FIG. 6: Cell adhesion and surface expression of CD11b on RAW 264.7 cells is not affected by retargeted BoNT/B. a) RAW 264.7 cells, treated with indicated conditions, were incubated with DiO and quantified with a fluorescent plate reader. Error bars represent SEM, n=8. b) Density plots of RAW 264.7 cells incubated with a FITC-CD11b antibody as analyzed by flow cytometry. Surface expression of CD11b was similar across all tested conditions.

To further investigate the effects of BoNT/B on macrophage recruitment, we investigated whether retargeted toxins affected integrin trafficking in RAW264.7 cells. Adhesion through β1 integrins and activation of CD11b are thought to be critical for differentiation of monocytes to macrophages. We observed no significant differences in adhesion between treated and untreated cells (FIG. 6A) or in CD11b surface expression (FIG. 6B). Thus, it is believed that the reduction in the level of intraperitoneal macrophages is largely due to the reduced extent of recruitment of monocytes and leukocytes because of decreased levels of TNFα.

The CNTs have proven to be invaluable tools to dissect the function of SNARE proteins in membrane fusion and neuroexocytosis; however, the study of SNAREs in noneuronal cells, especially in primary human immune cells, have been hampered by limitations regarding molecular approaches and the lack of effective delivery of CNTs into these cells. Therefore, the ability to retarget the CNTs brings into the immunology field a potent new tool to study the function of SNAREs in immune cells. Finally, uptake of the toxin, utilizing the ubiquitously expressed LDLR and Tr receptor, also provides the possibility to drive CNT entry into almost any cell type.

The CNTs are powerful therapeutic agents that reduce the symptoms of many profound diseases including cervical dystonia and migraine headache. The findings reported here demonstrate that these toxins can be engineered to target cells other than neurons. In particular, targeting the CNTs to human macrophages can help alleviate symptoms in many diseases such as rheumatoid arthritis, Crohn's disease, psoriasis and refractory asthma. Blocking the effects of TNFα has also been shown to inhibit tumor vascularization and the progression of atherosclerosis. Using the BoNT/BΔHC retargeting strategy described here, inhibition of TNFα takes place upstream of secretion and could be administrated locally to prevent the release of TNFα from human macrophages. With the added benefit of the prolonged effects of BoNT/B, this strategy introduces a powerful new class of therapeutics.

Example 2

BoNT/F Reduces EPO Release in Primary Human Eosinophils

Figure 5:
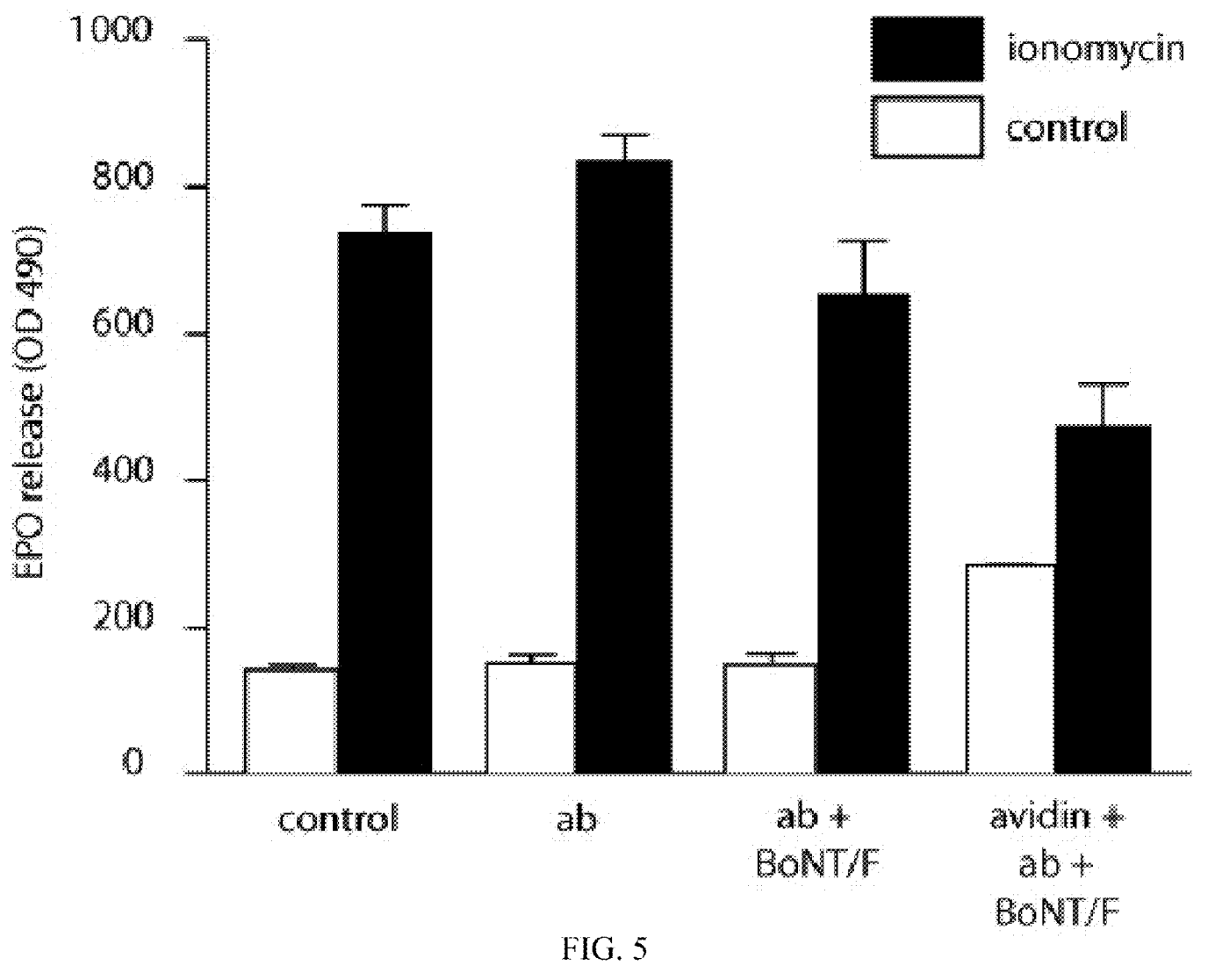

Referring to FIG. 5, human primary eosinophils were incubated in media with the addition of PBS (control), 3 μg of biotinylated CD11b antibody (ab), biotinylated BoNT/F (75 nM) with CD11b antibody (ab+BoNT/F pre-incubated with avidin and biotinylated CD11b antibody (avidin+ab+ BoNT/F). Cells were incubated at 37° C. for 24 hours. Eosinophil peroxidase (EPO) release was analyzed using a peroxidase assay in the absence of presence of ionomycin stimulation. We observed a decrease in ionomycin-induced EPO release in the presence of the pre-conjugated complex (avidin+ab+BoNT/F) as compared to control.

Example 3

Antibodies and Materials

This example describes antibodies of materials utilized in the above examples 1 and 2.

Monoclonal antibodies directed against syb II (Cl. 69.1), syp (Cl. 7.2), and SNAP-25 (Cl. 71.1) were generously provided by R. Jahn (Max-Planck-Institute for Biophysical Chemistry, Gottingen, Germany). Rabbit polyclonal antibodies against BoNT/A and BoNT/B were described previously. Rabbit anti-ceb, mouse anti-β-actin, and biotin labeled anti-LDLR antibodies were purchased from Abcam (Cambridge, Mass.).

TeNT was purchased from List Biological Laboratories (Campbell, Calif.). BoNT/A, BoNT/B, BoNT/E, and BoNT/F were purified as described previously. Chicken avidin, α-chymotrypsin VII, sodium thioglycollate broth, and human biotin-labeled Tr were purchased from Sigma-Aldrich (St. Louis, Mo.). The chicken avidin cDNA was generously provided by M. S. Kulomaa (University of Tampere, Finland).

Human recombinant macrophage colony-stimulating factor (M-CSF) and IFNα were purchased from PeproTech (Rock Hill, N.J.). LPS (Escherichia coli, serotype 0111:B4) was obtained from Sigma Chemical Co. (St. Louis, Mo.). MMP-9 and TNFα recombinant proteins standards and ELISA antibodies were obtained from R&D (Minneapolis, Minn.) and BD Biosciences (Franklin Lakes, N.J.), respectively. PE conjugated CD115 antibodies were purchased from eBioscience (San Diego, Calif.).

Preparation of BoNT/BΔHC and Biotinylation of Toxins

Biotinylation of toxin was performed as previously described. Digestion of BoNT/B holotoxin to create BoNT/BΔHC was performed in a manner similar to previous protocols. 50~100 μg of BoNT/B was incubated with chymotrypsin at a toxin to enzyme ratio of 50:1. The mixture was incubated at 37° C. and monitored every 3 days on an SDS-PAGE gel. This procedure was repeated until holotoxin was no longer detected by SDS-PAGE. PMSF (1 mM) was added to inhibit chymotrypsin activity.

Cell Culture and CNT Treatment Procedures

Transient transfection of HEK-293 cells performed with Lipofectamine 2000 according to manufacturer's protocol (Invitrogen, Carlsbad, Calif.). For the AvLDLR experiments, HEK-293 cells were transfected with an empty pEGFP-N1 vector or one containing the AvLDLR gene. Additionally, either SNAP-25b or syb II, in pIRES2-EGFP, was also introduced via transfection at a 1:2 DNA ratio compared to the pEGFP-N1 vector. One day post-transfection, cells were incubated with 5 nM biotin-CNT in serum free media for 8 h before serum was added to a final concentration of 10%. Cells were harvested 3 days post-transfection and lysates were subjected to immunoblot analysis. For the Tr experiments, biotin-CNTs were incubated with avidin and Tr at a 1:1.2:1.4 molar ratio, respectively. In the α-LDLR antibody experiments, 5 μl of antibody was used in place of Tr. Incubation procedures and analysis were performed as described for the AvLDLR experiments.

The murine RAW264.7 cell line was obtained from ATCC (Manassas, Va.) and cultured in RPMI 1640 with 5% cosmic calf serum (Hyclone Logan, Utah), 2 mM sodium pyruvate, 2 mM L-glutamine, and 100 units/ml penicillin/streptomycin. Cells were grown in 24-well plates with 0.5 ml medium and treated with 50 nM BoNT/B with or without antibodies (at a 1:1 molar ratio) for 6 h. Cells were subsequently stimulated with 500 pg/ml IFNα and 100 ng/ml LPS. After 48 h, cell lysates were collected and ceb cleavage was assessed via immunoblot analysis.

Human blood monocytes were purified from heparinized blood drawn from adult donors, as described previously. Briefly, blood was separated using a Percoll gradient and the monocyte layer recovered. Further enrichment of monocytes was performed through negative selection using a RosetteSep monocyte enrichment cocktail (Stemcell Technologies, BC) and lymphocyte separation media (Mediatech, VA). This procedure is in compliance with an approved human subject protocol through the University of Wisconsin Health Sciences Human Subjects Committee.

Purified monocytes were cultured in RPMI 1640 supplemented with 10% FBS (Hyclone Logan, Utah), 2 mM sodium pyruvate, 2 mM L-glutamine, and 100 units/ml penicillin/streptomycin. Monocytes were differentiated with 20 ng/ml M-CSF for 7 days. BoNT/B, with or without antibody, was added 6 h prior to stimulation with 10 ng/ml IFNα and 100 ng/ml LPS. After 48 hours, the supernatant was collected from each well and stored at −70° C. for subsequent cytokine analysis by ELISA. Cell lysates were collected and protein concentration was measured using a microBCA assay.

Rat hippocampal neurons were cultured as described previously. For BoNT/B and BoNT/BΔHC titration experiments, the indicated concentration of toxin was incubated with neurons for 48 hours. Neuronal lysates were harvested as described previously and cleavage of syb II was assessed via immunoblot analysis.

Mouse Peritoneal Injections and FACS Analysis

Adult C57/BL6 mice (18-22 g) were injected with a 3% sodium thioglycollate broth solution (400 µl) to induce macrophage enrichment in the peritoneal cavity. After four days, the mice were injected with 25 ng of BoNT/BΔHC, 42 ng of αB antibody, or a combination of both in 500 μl of sterile PBS. Control mice were injected with PBS alone. Mice were euthanized four hours later and cells within the intraperitoneal cavity were harvested. None of the mice exhibited any symptoms typical of botulinum poisoning and were healthy during the course of the experiment. Cells ($1\times10^5$) were incubated with 0.2 μg PE-CD115 or an isotype control antibody in FACS buffer (PBS with 0.25% BSA and 1 mM EDTA) for 30 min at 4° C. 10,000 events were collected using a BD Biosciences FACSCalibur flow cytometer (Flow Cytometry Facility, University of Wisconsin, Madison, Wis.) and CellQuest software (BD Biosciences). To determine the percentage of CD-115 positive macrophages, dead cells were gated out (marked by propidium iodide) before creating density plots of the remaining cells. A tight region was set to encompass PE-CD115 positive cells, but not cells incubated with the control antibody. Total macrophages were determined by the total peritoneal cells× percentage of CD115 positive cells.

ELISA and MTS Assays

A sandwich ELISA was performed to analyze TNFα and MMP9 secretion. The assay was developed using streptavidin conjugated to an HRP polymer, POLY-HRP-40 (Fitzgerald Industries, MA) and a one-component substrate, 3,3',5'5'-tetramethylbenzidine (BioFx Laboratories, MD). Color development was stopped by the addition of 0.18 M sulfuric acid. The absorbance at 450 nm was measured using an ELx800 universal microplate reader and data were analyzed with Ascent Software. The protein concentration was determined according to a standard curve using recombinant proteins.

Human BMDMs were stimulated as indicated and supernatants were collected for ELISA. Cell viability was assessed using the nonradioactive cell proliferation assay (3-4,5-dimethylthiazol-2-yl)-5-(3-carboxymethoxyphenyl)-2-(4-sulfophenyl)-2H-tetrazolium salt [MTS]-based assay; Promega, Madison, Wis.), according to the manufacturer's protocol.

Statistical Methods

Statistical significance was evaluated by two-tailed unpaired Student's t-test: *$p<0.05$, $p<0.01$, *$p<0.001$.

Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference. It is understood that the invention is not confined to the specific reagents, formulations, reaction conditions, etc., herein illustrated and described, but embraces such modified forms thereof as come within the scope of the following claims.

REFERENCES

1. Jankovic, J. Botulinum toxin in clinical practice. *J Neurol Neurosurg Psychiatry* 75, 951-957 (2004).
2. Russo, C. & Polosa, R. TNF-alpha as a promising therapeutic target in chronic asthma: a lesson from rheumatoid arthritis. *Clin Sci* (*Lond*) 109, 135-142 (2005).
3. Meng, Y., et al. Blockade of tumor necrosis factor alpha signaling in tumor-associated macrophages as a radiosensitizing strategy. *Cancer Res* 70, 1534-1543 (2010).
4. Kleemann, R., Zadelaar, S. & Kooistra, T. Cytokines and atherosclerosis: a comprehensive review of studies in mice. *Cardiovasc Res* 79, 360-376 (2008).
5. Murray, R. Z., Kay, J. G., Sangermani, D. G. & Stow, J. L. A role for the phagosome in cytokine secretion. *Science* 310, 1492-1495 (2005).
6. Stow, J. L., Manderson, A. P. & Murray, R. Z. SNAREing immunity: the role of SNAREs in the immune system. *Nat Rev Immunol* 6, 919-929 (2006).
7. Schiavo, G., Matteoli, M. & Montecucco, C. Neurotoxins affecting neuroexocytosis. *Physiol Rev* 80, 717-766 (2000).
8. Aoki, K. R. Review of a proposed mechanism for the antinociceptive action of botulinum toxin type A. *Neurotoxicology* 26, 785-793 (2005).
9. Dolly, J. O. & Aoki, K. R. The structure and mode of action of different botulinum toxins. *Eur J* Neurol 13 Suppl 4, 1-9 (2006).
10. Chapman, E. R. How does synaptotagmin trigger neurotransmitter release? *Annu Rev Biochem* 77, 615-641 (2008).
11. Rossetto, O., et al. VAMP/synaptobrevin isoforms 1 and 2 are widely and differentially expressed in nonneuronal tissues. *J Cell Biol* 132, 167-179 (1996).
12. Davis, C. W. & Dickey, B. F. Regulated airway goblet cell mucin secretion. *Annu Rev Physiol* 70, 487-512 (2008).
13. Janz, R., Goda, Y., Geppert, M., Missler, M. & Sudhof, T. C. SV2A and SV2B function as redundant Ca2+ regulators in neurotransmitter release. *Neuron* 24, 1003-1016 (1999).
14. Geppert, M., Archer, B. T., 3rd & Sudhof, T. C. Synaptotagmin II. A novel differentially distributed form of synaptotagmin. *J Biol Chem* 266, 13548-13552 (1991).
15. Rummel, A., Karnath, T., Henke, T., Bigalke, H. & Binz, T. Synaptotagmins I and II act as nerve cell receptors for botulinum neurotoxin G. *J Biol Chem* 279, 30865-30870 (2004).
16. Mahrhold, S., Rummel, A., Bigalke, H., Davletov, B. & Binz, T. The synaptic vesicle protein 2C mediates the uptake of botulinum neurotoxin A into phrenic nerves. *FEBS Lett* 580, 2011-2014 (2006).
17. Dong, M., et al. SV2 is the protein receptor for botulinum neurotoxin A. *Science* 312, 592-596 (2006).
18. Dong, M., Tepp, W. H., Liu, H., Johnson, E. A. & Chapman, E. R. Mechanism of botulinum neurotoxin B and G entry into hippocampal neurons. *J Cell Biol* 179, 1511-1522 (2007).
19. Dong, M., et al. Glycosylated SV2A and SV2B mediate the entry of botulinum neurotoxin E into neurons. *Mol Biol Cell* 19, 5226-5237 (2008).
20. Yeh, F. L., et al. SV2 Mediates Entry of Tetanus Neurotoxin into Central Neurons. *PLoS Pathog* 6, e1001207 (2010).
21. Lehtolainen, P., et al. Targeting of biotinylated compounds to its target tissue using a low-density lipoprotein receptor-avidin fusion protein. *Gene Ther* 10, 2090-2097 (2003).

22. Fujihara, S., et al. Inhibition of NF-kappa B by a cell permeable form of I kappa B alpha induces apoptosis in eosinophils. *Biochem Biophys Res Commun* 326, 632-637 (2005).
23. Moulding, D. A., Quayle, J. A., Hart, C. A. & Edwards, S. W. Mcl-1 expression in human neutrophils: regulation by cytokines and correlation with cell survival. *Blood* 92, 2495-2502 (1998).
24. Kaplan, J. Mechanisms of cellular iron acquisition: another iron in the fire. *Cell* 111, 603-606 (2002).
25. Mosser, D. M. & Edwards, J. P. Exploring the full spectrum of macrophage activation. *Nat Rev Immunol* 8, 958-969 (2008).
26. Helting, T. B., Ronneberger, H. J., Vollerthun, R. & Neubauer, V. Toxicity of papain-digested tetanus toxin. Pathological effect of fragment B in the absence of spastic paralysis. *J Biol Chem* 253, 125-129 (1978).
27. Chaddock, J. A., et al. Expression and purification of catalytically active, non-toxic endopeptidase derivatives of *Clostridium botulinum* toxin type A. *Protein Expr Purif* 25, 219-228 (2002).
28. Kozaki, S., Ogasawara, J., Shimote, Y., Kamata, Y. & Sakaguchi, G. Antigenic structure of *Clostridium botulinum* type B neurotoxin and its interaction with gangliosides, cerebroside, and free fatty acids. *Infect Immun* 55, 3051-3056 (1987).
29. Mollinedo, F., Martin-Martin, B., Calafat, J., Nabokina, S. M. & Lazo, P. A. Role of vesicle-associated membrane protein-2, through Q-soluble N-ethylmaleimide-sensitive factor attachment protein receptor/R-soluble N-ethylmaleimide-sensitive factor attachment protein receptor interaction, in the exocytosis of specific and tertiary granules of human neutrophils. *J Immunol* 170, 1034-1042 (2003).
30. Gavala, M. L., Pfeiffer, Z. A. & Bertics, P. J. The nucleotide receptor P2RX7 mediates ATP-induced CREB activation in human and murine monocytic cells. *J Leukoc Biol* 84, 1159-1171 (2008).

What is claimed is:

1. A method for selectively targeting a bacterial toxin to a cell, comprising contacting a cell with a toxic bioactive fragment of a bacterial toxin associated with an antibody or ligand that is specific to a target protein on the cell, wherein the toxic bioactive fragment is associated with the antibody or ligand by an avidin/biotin or streptavidin/biotin linkage, wherein the antibody is selected from the group consisting of a low density lipoprotein receptor antibody, a transferrin receptor antibody, and a vesicular dopamine transport antibody, wherein the toxic bioactive fragment is the enzymatic domain of the bacterial toxin and lacks a functional receptor binding domain; whereby the toxic bioactive fragment is internalized and enters the cell upon selective binding of the antibody or ligand to the target protein.

2. The method according to claim 1, wherein the bacterial toxin is a *clostridium* neurotoxin.

3. The method according to claim 1, wherein the bacterial toxin is selected from the group consisting of botulinum neurotoxin A (BoNT/A), botulinum neurotoxin B (BoNT/B), botulinum neurotoxin C (BoNT/C), botulinum neurotoxin D (BoNT/D), botulinum neurotoxin E (BoNT/E), botulinum neurotoxin F (BoNT/F), botulinum neurotoxin G (BoNT/G), tetanus neurotoxin (TeNT), Diphtheria toxin, and *Pseudomonas* exotoxin.

4. The method according to claim 1, wherein the target protein is a plasma membrane protein or a protein located at a plasma membrane of the cell.

5. The method according to claim 1, wherein the target protein is a receptor protein.

6. The method according to claim 1, wherein the target protein is a protein located at a secretory vesicle of the cell.

7. The method according to claim 1, wherein the target protein is a component of the cell's complement system and entry is mediated by said complement system.

8. The method according to claim 1, wherein the cell is an immune cell, a neuronal cell, an exocrine gland cell, or an endocrine gland cell.

9. The method according to claim 1, wherein the cell is a cancer or tumor cell.

10. The method according to claim 1, wherein the cell is contained in a subject.

* * * * *

UNITED STATES PATENT AND TRADEMARK OFFICE
CERTIFICATE OF CORRECTION

PATENT NO. : 9,623,117 B2
APPLICATION NO. : 13/435688
DATED : April 18, 2017
INVENTOR(S) : Edwin Raymond Chapman et al.

It is certified that error appears in the above-identified patent and that said Letters Patent is hereby corrected as shown below:

In the Specification

Column 4, Line 49, "(1)" should be --(f)--.

Column 5, Line 12, "FIN" should be --HN--.

Column 8, Line 45, "permeabilized" should be --permeablized--.

Signed and Sealed this
Eighteenth Day of July, 2017

Joseph Matal
*Performing the Functions and Duties of the*
*Under Secretary of Commerce for Intellectual Property and*
*Director of the United States Patent and Trademark Office*